(12) United States Patent
Yu et al.

(10) Patent No.: US 9,968,644 B2
(45) Date of Patent: May 15, 2018

(54) TRADITIONAL CHINESE MEDICINE COMPOSITION FOR SOBER-UP AND HEPATIC PROTECTION AND A PROCESS FOR PREPARING THE SAME

(71) Applicant: INFINITUS (CHINA) COMPANY LTD., Jiang Men (CN)

(72) Inventors: Qingtao Yu, Jiang Men (CN); Yazhong Ge, Jiang Men (CN); Chung Wah Ma, Jiang Men (CN); Wai Sum Lee, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 128 days.

(21) Appl. No.: 15/091,954

(22) Filed: Apr. 6, 2016

(65) Prior Publication Data
US 2016/0310554 A1 Oct. 27, 2016

(30) Foreign Application Priority Data
Apr. 27, 2015 (CN) .......................... 2015 1 0209657

(51) Int. Cl.
| | | |
|---|---|---|
| *A61K 36/744* | (2006.01) |
| *A61K 36/488* | (2006.01) |
| *A61K 36/72* | (2006.01) |
| *A61K 9/00* | (2006.01) |
| *A61K 9/14* | (2006.01) |
| *A61K 9/20* | (2006.01) |
| *A61K 9/48* | (2006.01) |
| *A61K 9/50* | (2006.01) |

(52) U.S. Cl.
CPC .......... *A61K 36/744* (2013.01); *A61K 9/0056* (2013.01); *A61K 9/0095* (2013.01); *A61K 9/145* (2013.01); *A61K 9/2054* (2013.01); *A61K 9/4866* (2013.01); *A61K 9/5031* (2013.01); *A61K 36/488* (2013.01); *A61K 36/72* (2013.01)

(58) Field of Classification Search
CPC ...................................................... A61K 36/00
See application file for complete search history.

(56) References Cited

FOREIGN PATENT DOCUMENTS

CN 103315356 A * 9/2013

* cited by examiner

*Primary Examiner* — Qiuwen Mi
(74) *Attorney, Agent, or Firm* — Parker Highlander PLLC

(57) ABSTRACT

The present invention relates to traditional Chinese medicine, particularly to a traditional Chinese medicine composition for sober-up and hepatic protection and a process for preparing the same. This composition is made from Radix Puerariae, Semen Hoveniae and Fructus Gardeniae. This composition has no significant effect on the body weight of mice. The hepatic TG level in animals of 1.400 g/kg·bw dosage group is significantly lower than that of the model control group, while the hepatic GSH level is significantly higher than that of the model control group. The degree of hepatic steatosis in animals of 1.400 g/kg·bw dosage group is significantly lower than that of the model control group. Therefore, the composition of the present invention has auxiliary protective effects on liver damages caused by alcohol. The process for preparing the composition comprises: extracting Radix Puerariae, Semen Hoveniae and Fructus Gardeniae with water, concentrating, drying, and pulverizing the extract.

6 Claims, No Drawings ated to US 9,968,644 B2

TRADITIONAL CHINESE MEDICINE COMPOSITION FOR SOBER-UP AND HEPATIC PROTECTION AND A PROCESS FOR PREPARING THE SAME

This application claims the benefit of priority to Chinese Patent Application No. 201510209657.3, filed Apr. 27, 2015. The entire content of the above-referenced disclosure is specifically incorporated herein by reference.

FIELD OF THE INVENTION

The present invention relates to the technical field of traditional Chinese medicine, particularly to a traditional Chinese medicine composition for sober-up and hepatic protection and a process for preparing the same.

BACKGROUND OF THE INVENTION

Wine is a mixture of various chemical ingredients, mainly alcohol and water, as well as numerous chemical substances such as acids, esters, aldehydes, alcohols, carbohydrates, proteins, inorganic salts, trace elements, pectins, and various vitamins, etc. China is the hometown of wine, and has its wine culture for a long history since ancient times. The Chinese wine has a long history of more than 5,000 years, and forms its unique style. The ancient Chinese classified the effects of wine into the following aspects: treating diseases, providing for the aged, presenting as gifts, pursuing pleasure, forgetting worry, emboldening, and also wallowing, corrupting, hurting physical health, etc.

In modern China, hundreds of millions of tons of wine are produced every year, with sales of up to hundreds of billions of RMB. The varieties of wine are much more abundant than before. There is also some development in the wine culture. So to speak, everyone drinks some wine, and thus wine has long been integrated into our social and economic life. In business occasions, gathering of friends and various dinner parties, it is conventional to drink some wine for celebration. However, after wine drinking, symptoms such as dizziness, fullness in head, blush, vomit, parched mouth and scorched tongue, systemic fever would appear. Modern scientific studies have shown that long-term excessive drinking of wine has the following main harms: long-term excessive drinking of wine can cause steatosis, inflammatory necrosis and fibrosis of liver cells, and ultimately lead to alcoholic liver diseases including alcoholic hepatitis, alcoholic fatty liver, alcoholic liver cirrhosis, liver failure, and most seriously, lead to liver cancer.

Whether a person is drunk depends on the ethanol concentration in the blood. Due to different abilities of gastrointestinal absorption and hepatic metabolic treatment, the tolerance to ethanol differs much from person to person. Therefore, products capable of promoting decomposition of alcohol in liver are usually taken to achieve the sober-up and hepatic protection purpose. The sober-up products are generally divided into three categories: chemical drugs, traditional Chinese medicine preparations, and health care products. However, there is still an urgent need for effective sober-up and hepatic protection products.

SUMMARY OF THE INVENTION

In view of the above, the technical problem to be solved by the present invention is to provide a traditional Chinese medicine composition that can effectively sober up and protect the liver as well as relieve drunkenness symptoms, and a process for preparing the same.

The traditional Chinese medicine composition for sober-up and hepatic protection of the present invention is made from the following raw materials: Radix Puerariae, Semen Hoveniae and Fructus Gardeniae.

In the present invention, after intragastric gavage to mice with 0.233 g/kg·bw, 0.467 g/kg·bw, 1.400 g/kg·bw of the traditional Chinese medicine composition for sober-up and hepatic protection for 30 days, acute liver damage model is established with ethanol. The result shows that the traditional Chinese medicine composition of the present invention has no significant effect on the body weight of mice. The hepatic TG level in animals of 1.400 g/kg·bw dosage group is significantly lower than that of the model control group, while the hepatic GSH level is significantly higher than that of the model control group, and the difference is significant ($p<0.05$ or $p<0.01$). The degree of hepatic steatosis in animals of 1.400 g/kg·bw dosage group is significantly lower than that of the model control group, and the difference is significant ($p<0.05$). Thus, it is demonstrated that the traditional Chinese medicine composition of the present invention has auxiliary protective effects on liver damages caused by alcohol.

In the examples of the present invention, the traditional Chinese medicine composition is made from raw materials in the following parts by mass: 6 parts to 12 parts of Radix Puerariae, 3 parts to 6 parts of Semen Hoveniae, and 1 part to 3 parts of Fructus Gardeniae.

In the examples of the present invention, the traditional Chinese medicine composition is made from raw materials in the following parts by mass: 8 parts to 10 parts of Radix Puerariae, 4 parts to 5 parts of Semen Hoveniae, and 1.5 parts to 2.5 parts of Fructus Gardeniae.

In some examples, the traditional Chinese medicine composition is made from raw materials in the following parts by mass: 8 parts of Radix Puerariae, 4 parts of Semen Hoveniae, and 1.5 parts of Fructus Gardeniae.

In some examples, the traditional Chinese medicine composition is made from raw materials in the following parts by mass: 8 parts of Radix Puerariae, 4 parts of Semen Hoveniae, and 2.5 parts of Fructus Gardeniae.

In some examples, the traditional Chinese medicine composition is made from raw materials in the following parts by mass: 8 parts of Radix Puerariae, 5 parts of Semen Hoveniae, and 2.5 parts of Fructus Gardeniae.

In some examples, the traditional Chinese medicine composition is made from raw materials in the following parts by mass: 8 parts of Radix Puerariae, 5 parts of Semen Hoveniae, and 1.5 parts of Fructus Gardeniae.

In some examples, the traditional Chinese medicine composition is made from raw materials in the following parts by mass: 10 parts of Radix Puerariae, 5 parts of Semen Hoveniae, and 2.5 parts of Fructus Gardeniae.

In some examples, the traditional Chinese medicine composition is made from raw materials in the following parts by mass: 10 parts of Radix Puerariae, 4 parts of Semen Hoveniae, and 1.5 parts of Fructus Gardeniae.

In some examples, the traditional Chinese medicine composition is made from raw materials in the following parts by mass: 10 parts of Radix Puerariae, 4 parts of Semen Hoveniae, and 2.5 parts of Fructus Gardeniae.

In some examples, the traditional Chinese medicine composition is made from raw materials in the following parts by mass: 10 parts of Radix Puerariae, 5 parts of Semen Hoveniae, and 1.5 parts of Fructus Gardeniae.

In some examples, the traditional Chinese medicine composition is made from raw materials in the following parts by mass: 6 parts of Radix Puerariae, 3 parts of Semen Hoveniae, and 1 parts of Fructus Gardeniae.

In some examples, the traditional Chinese medicine composition is made from raw materials in the following parts by mass: 6 parts of Radix Puerariae, 6 parts of Semen Hoveniae, and 3 parts of Fructus Gardeniae.

In some examples, the traditional Chinese medicine composition is made from raw materials in the following parts by mass: 6 parts of Radix Puerariae, 6 parts of Semen Hoveniae, and 1 parts of Fructus Gardeniae.

In some examples, the traditional Chinese medicine composition is made from raw materials in the following parts by mass: 6 parts of Radix Puerariae, 3 parts of Semen Hoveniae, and 3 parts of Fructus Gardeniae.

In some examples, the traditional Chinese medicine composition is made from raw materials in the following parts by mass: 12 parts of Radix Puerariae, 3 parts of Semen Hoveniae, and 1 parts of Fructus Gardeniae.

In some examples, the traditional Chinese medicine composition is made from raw materials in the following parts by mass: 12 parts of Radix Puerariae, 6 parts of Semen Hoveniae, and 3 parts of Fructus Gardeniae.

In some examples, the traditional Chinese medicine composition is made from raw materials in the following parts by mass: 12 parts of Radix Puerariae, 6 parts of Semen Hoveniae, and 1 part of Fructus Gardeniae.

In some examples, the traditional Chinese medicine composition is made from raw materials in the following parts by mass: 12 parts of Radix Puerariae, 3 parts of Semen Hoveniae, and 3 parts of Fructus Gardeniae.

Preferably, the traditional Chinese medicine composition is made from raw materials in the following parts by mass: 9 parts of Radix Puerariae, 4.5 parts of Semen Hoveniae, and 2 parts of Fructus Gardeniae.

Radix Puerariae is the dried root of *Pueraria lobata* (Willd.) Ohwi from Leguminosae. It tastes sweet, pungent, is cool in nature and attributed to the lung and stomach meridians. It has the effects of relieving superficies and clearing heat, promoting fluid production, promoting eruption, promoting yang rising and stopping diarrhea. It is indicated for exogenous fever and headache, hypertension neck pain, thirst, diabetes, measles without adequate eruption, heat dysentery, and diarrhea.

Semen Hoveniae is the fruit with fleshy fruit stalk or seed of *Hovenia acerba* Lindl from Rhamnaceae. It tastes sweet, sour, and is calm in nature. It can be used for clearing heat and inducing diuresis, relieving cough and restlessness, and relieving alcoholism.

Fructus Gardeniae is the fruit of *Gardenia Jasminoides* Eillis from Rubiaceae. It tastes bitter, is cold in nature and attributed to the heart, lung & triple energy meridians. It has the effects of hepatic protection, choleresis, antihypertension, sedation, hemostasis, detumescence, etc.

After extraction of Radix Puerariae, Semen Hoveniae and Fructus Gardeniae, the obtained product contains plenty of flavonoids. Flavonoids are widely distributed in plants, and have various biological activities, such as anti-bacterial & anti-virus activity, anti-tumor activity, treating cardiovascular & cerebrovascular diseases, anti-oxidant activity, anti-inflammatory & analgesic activity, hepatic protection activity, etc. Tests have shown that, in the traditional Chinese medicine composition prepared and obtained by employing the process provided in the present invention, the content of flavonoids is 800 mg/100 g to 1400 mg/100 g.

The process for preparing the traditional Chinese medicine composition of the present invention comprises: extracting Radix Puerariae, Semen Hoveniae and Fructus Gardeniae with water, concentrating, drying, and pulverizing the extract to obtain the traditional Chinese medicine composition for sober-up and hepatic protection.

In some examples, the mass of water in the extraction is 8 to 12 times the sum of the mass of Radix Puerariae, Semen Hoveniae and Fructus Gardeniae.

Preferably, the mass of water is 10 times the sum of the mass of Radix Puerariae, Semen Hoveniae and Fructus Gardeniae.

In some examples, the extraction is carried out by way of decoction.

Preferably, the decoction is carried out twice, each for 2 hours.

In some examples, the concentration is conducted to achieve a relative density of 1.0 to 1.5.

Preferably, the concentration is conducted to achieve a relative density of 1.2.

In the examples of the present invention, the relative density is measured at 60° C.

In some examples, the concentration is conducted under normal pressure or reduced pressure.

In some examples, the drying is conducted to achieve a moisture content ≤6%.

Preferably, the pulverizing is conducted to achieve a particle size of 60 mesh to 100 mesh.

Specifically, the process for preparing the composition for sober-up and hepatic protection of the present invention comprises:

step 1: placing the Radix Puerariae, Semen Hoveniae and Fructus Gardeniae into a extraction pot, conducting decoction twice with 10 times of water, each for 2 hours, extracting and filtering, and combining to obtain an extract solution;

step 2: concentrating the extract solution to achieve a relative density of 1.0 to 1.5, to obtain a concentrated solution;

step 3: drying the concentrated solution at 60° C. to 85° C. to a moisture content ≤5%, pulverizing, passing through a 60 mesh to 100 mesh sieve, to obtain the traditional Chinese medicine composition for sober-up and hepatic protection.

In the examples of the present invention, in the traditional Chinese medicine composition for sober-up and hepatic protection of the present invention, the content of flavonoids is 800 mg/100 g to 1400 mg/100 g.

Preferably, the traditional Chinese medicine composition for sober-up and hepatic protection is administered at a dosage of 0.0467 g/kg·bw.

An oral preparation for easy intake can be prepared by mixing the traditional Chinese medicine composition for sober-up and hepatic protection of the present invention with a pharmaceutically acceptable excipient.

The present invention further provides a sober-up and hepatic protection medication comprising the traditional Chinese medicine composition for sober-up and hepatic protection of the present invention and a pharmaceutically acceptable excipient.

In some examples provided in the present invention, the pharmaceutically acceptable excipient is one or a mixture of two or more from fruit powder, edible essence, sweetener, acidulant, filler, lubricant, preservative, suspending agent, edible pigment, diluent, emulsifier, disintegrant, or plasticizer.

Preferably, the fruit powder is one or a mixture of two or more selected from tangerine powder, orange powder, lemon powder, cherry powder, apple powder, or coconut powder. However, all the fruit powders deemed feasible by those skilled in the art are within the scope of the present invention. The species of the fruit power are not limited hereto, and are not defined in the present invention here.

Preferably, the edible essence is one or a mixture of two or more from tangerine essence, orange essence, lemon essence, cherry essence, menthol, apple essence, or coconut essence. However, all the edible essences deemed feasible by those skilled in the art are within the scope of the present invention. The species of the edible essence are not limited hereto, and are not defined in the present invention here.

In order to enhance the mouthfeel of the health care product, sweeteners can further be added to enhance the sweetness of the health care product. Preferably, the sweetener is one or a mixture of two or more from sucralose, AK sugar, aspartame, or mogroside. However, all the sweeteners deemed feasible by those skilled in the art are within the scope of the present invention. The species of the sweetener are not limited hereto, and are not defined in the present invention here.

Preferably, the acidulant is one or a mixture of two or more from citric acid, malic acid, lactic acid, or citric acid. However, all the acidulants deemed feasible by those skilled in the art are within the scope of the present invention. The species of the acidulant are not limited hereto, and are not defined in the present invention here.

Filler refers to an excipient for increasing the weight and volume of a tablet to facilitate tablet compression. Fillers used in a tablet should possess good flowability and compressibility, strong binding force, and greater carrying capacity for drugs. Preferably, the filler is one or a mixture of two or more from fructose, sugar alcohols, sucrose, starch, pregelatinized starch, microcrystalline cellulose, or dextrin. However, all the fillers deemed feasible by those skilled in the art are within the scope of the present invention. The species of the filler are not limited hereto, and are not defined in the present invention here.

Lubricant refers to an excipient capable of reducing the friction between the tablet and the wall of the punch die to prevent the difficulty in tablet compression due to high friction. It can render distribution of the tablet compression force more uniform, achieve a uniform density of the tablet, and can also improve the appearance of the tablet, so as to render the surface of the tablet bright and smooth. Preferably, the lubricant is one or a mixture of two or more from talc, magnesium stearate, silicone dioxide, or stearic acid. However, all the lubricants deemed feasible by those skilled in the art are within the scope of the present invention. The species of the lubricant are not limited hereto, and are not defined in the present invention here.

Preferably, the preservative is one or a mixture of two or more from sodium benzoate, potassium benzoate, methyl sorbate, ethyl p-hydroxybenzoate, or phenyl p-hydroxybenzoate. However, all the preservatives deemed feasible by those skilled in the art are within the scope of the present invention. The species of the preservative are not limited hereto, and are not defined in the present invention here.

Preferably, the suspending agent is one or a mixture of two or more from sodium carboxymethyl cellulose, sodium alginate, or beeswax. However, all the suspending agents deemed feasible by those skilled in the art are within the scope of the present invention. The species of the suspending agent are not limited hereto, and are not defined in the present invention here.

Preferably, the edible pigment is one or a mixture of two or more from caramel colour, *gardenia* yellow, curcumin, or chlorophyll. However, all the edible pigments deemed feasible by those skilled in the art are within the scope of the present invention. The species of the edible pigment are not limited hereto, and are not defined in the present invention here.

Preferably, the diluent is one or a mixture of two or more from edible vegetable oil, propylene glycol, or polyethylene glycol having a molecular weight of 400 to 6000. However, all the diluents deemed feasible by those skilled in the art are within the scope of the present invention. The species of the diluent are not limited hereto, and are not defined in the present invention here.

Preferably, the emulsifier is one or a mixture of two or more from S-40, sodium/calcium stearyl lactate, diacetyl tartaric acid ester of monoglyceride, sucrose fatty acid ester, polyethylene glycol having a molecular weight of 400 to 6000, or distilled monoglyceride. However, all the emulsifiers deemed feasible by those skilled in the art are within the scope of the present invention. The species of the emulsifier are not limited hereto, and are not defined in the present invention here.

The disintegrant mainly functions to eliminate the binding force caused by binding agent or pressure during formation of the tablet, so as to rapidly disintegrate the tablet, and enable the tablet to rapidly take effect. Preferably, the disintegrant is one or a mixture of two or more from dry starch, sodium carboxymethyl starch, low-substituted hydroxypropyl cellulose, crosslinked polyvinylpyrrolidone, or sodium carboxymethyl cellulose. However, all the disintegrants deemed feasible by those skilled in the art are within the scope of the present invention. The species of the disintegrant are not limited hereto, and are not defined in the present invention here.

Preferably, the plasticizer is one or a mixture of two or more from glycerol, sodium carboxymethyl cellulose, sorbitol, or oleamide sodium sulfonate. However, all the plasticizers deemed feasible by those skilled in the art are within the scope of the present invention. The species of the plasticizer are not limited hereto, and are not defined in the present invention here.

Preferably, the sober-up and hepatic protection medication is in a dosage form of tablet, pill, oral liquid, capsule, syrup, dripping pill, or granule.

In some examples provided in the present invention, the capsule is hard capsule or soft capsule.

In some examples provided in the present invention, the tablet is oral tablet or buccal tablet.

Oral tablet refers to tablets for oral administration. Most of the drugs in such tablets take effect via absorption through gastrointestinal tract, while some of the drugs in tablets take effect locally in the gastrointestinal tract. In some examples provided in the present invention, the oral tablet is normal compressed tablet, dispersible tablet, effervescent tablet, chewable tablet, coated tablet, or sustained release and controlled release tablets.

Preferably, the formula for a sober-up and hepatic protection capsule is: 90 parts of the traditional Chinese medicine composition for sober-up and hepatic protection, 7 parts of corn starch, and 3 parts of magnesium stearate.

Preferably, the formula for a sober-up and hepatic protection normal compressed tablet is: 85 parts of the traditional Chinese medicine composition for sober-up and hepatic protection, 10 parts of microcrystalline cellulose, 1 part of sodium carboxymethyl cellulose, 2 parts of magnesium stearate, and 2 parts of 7% starch slurry.

Preferably, the formula for a sober-up and hepatic protection chewable tablet is: 78 parts of the traditional Chinese medicine composition for sober-up and hepatic protection, 20 parts of microcrystalline cellulose, 2 parts of mannitol, 0.6 part of aspartame, and 0.7 part of orange essence.

Preferably, the formula for sober-up and hepatic protection granules is: 90 parts of the traditional Chinese medicine composition for sober-up and hepatic protection, 5 parts of sucrose, and 5 parts of β-cyclodextrin.

Preferably, the formula for a sober-up and hepatic protection syrup is: 50 parts of the traditional Chinese medicine composition for sober-up and hepatic protection, 50 parts of sucrose, 100 parts of water, and 0.3 part of potassium sorbate.

Preferably, the formula for a sober-up and hepatic protection oral liquid is: 50 parts of the traditional Chinese medicine composition for sober-up and hepatic protection, 25 parts of simple syrup, 75 parts of water, and 0.3 part of potassium sorbate.

In some examples provided in the present invention, the formula for a sober-up and hepatic protection dripping pill is: 50 parts to 85 parts of the traditional Chinese medicine composition for sober-up and hepatic protection, and 15 parts to 50 parts of base.

Preferably, the base is a mixture of diluent and emulsifier.

In some examples provided in the present invention, the diluent is PEG6000.

In some examples provided in the present invention, the emulsifier is S-40.

Preferably, the formula for a sober-up and hepatic protection dripping pill is: 80 parts to 85 parts of the traditional Chinese medicine composition for sober-up and hepatic protection, 5 parts to 15 parts of PEG6000, and 3 parts to 10 parts of S-40.

Preferably, the formula for a sober-up and hepatic protection dripping pill is: 85 parts of the traditional Chinese medicine composition for sober-up and hepatic protection, 10 parts of PEG6000, and 5 parts of S-40.

In the above-mentioned dosage forms, the dripping pill has advantages of rapid onset, high efficacy and long-lasting efficacy. It is administered sublingually, and directly absorbed through sublingual mucosa into blood circulation, so as to avoid liver first-pass effect upon swallowing and degradation loss of the drug in the stomach, so that the drug reaches the target organ at high concentration and rapidly takes effect. Generally, only 5 to 15 minutes and at most 30 minutes are needed for it to take effect after sublingual administration. Furthermore, the dripping pill generally has a small volume, and is very convenient to carry. Currently, there is still no commercially available sober-up and hepatic protection dripping pill. Preparation of the sober-up and hepatic protection medication into dripping pills with the advantage of rapid onset not only is convenient for daily administration and carrying, but also can rapidly achieve the hepatic protection and sober-up effect under situations where drinking wine is suddenly required.

The traditional Chinese medicine composition for sober-up and hepatic protection of the present invention is made from the following raw materials: Radix Puerariae, Semen Hoveniae and Fructus Gardeniae. The traditional Chinese medicine composition of the present invention has no significant effect on the body weight of mice. After intragastric administration to mice with 0.233 g/kg·bw, 0.467 g/kg·bw, 1.400 g/kg·bw of the traditional Chinese medicine composition for sober-up and hepatic protection for 30 days, acute liver damage model is established with ethanol. The results suggest that the hepatic TG level in animals of 1.400 g/kg·bw dosage group is significantly lower than that of the model control group, while the hepatic GSH level is significantly higher than that of the model control group, and the difference is significant ($p<0.05$ or $p<0.01$). The degree of hepatic steatosis in animals of 1.400 g/kg·bw dosage group is significantly lower than that of the model control group, and the difference is significant ($p<0.05$). Thus, it is demonstrated that the traditional Chinese medicine composition of the present invention has auxiliary protective effects on liver damages caused by alcohol. The process for preparing the traditional Chinese medicine composition of the present invention comprises: extracting Radix Puerariae, Semen Hoveniae and Fructus Gardeniae with water, concentrating, drying, and pulverizing the extract to obtain the traditional Chinese medicine composition for sober-up and hepatic protection. Tests showed that, in the traditional Chinese medicine composition prepared and obtained by employing the process provided in the present invention, the content of flavonoids is 800 mg/100 g to 1400 mg/100 g.

DETAILED DESCRIPTION OF THE INVENTION

The present invention provides a traditional Chinese medicine composition for sober-up and hepatic protection and a process for preparing the same, which can be implemented by those skilled in the art by using the contents herein for reference and appropriately improving the process parameters. It is to be particularly noted that all the similar substitutions and modifications are obvious to those skilled in the art, and should be deemed to be within the present invention. The process and use have been described by preferred examples. Related personnel can obviously implement and apply the technology of the present invention by modifying or appropriately altering and combining the process and use herein without departing from the disclosure, spirit and scope of the present invention.

All the instruments employed in the present invention are general commercially available products, which can be purchased commercially.

The present invention will be further illustrated in conjunction with the following examples.

Examples 1 to 17. Preparation of the Traditional Chinese Medicine Composition for Sober-Up and Hepatic Protection Radix Puerariae, Semen Hoveniae and Fructus Gardeniae were placed into an extraction pot, decocted twice with 8 to 12 times by mass of water, each for 2 hours. The mixture was filtered after extraction. The filtrates were pooled to obtain the extract solution.

The extract solution was concentrated to a relative density of 1.0 to 1.5 to obtain a concentrated solution.

The concentrated solution was dried to a moisture content ≤5%. The obtained solid was pulverized and passed through a 60 mesh to 100 mesh sieve to obtain the traditional Chinese medicine composition for sober-up and hepatic protection.

The amount used for Radix Puerariae, Semen Hoveniae, Fructus Gardeniae, and water is shown in Table 1:

TABLE 1

Examples 1 to 17

| Example No. | Radix Puerariae (g) | Semen Hoveniae (g) | Fructus Gardeniae (g) | Water (g)/time | Content of flavonoids (mg/100 g) |
|---|---|---|---|---|---|
| 1 | 8 | 4 | 1.5 | 135 | 1135 |
| 2 | 8 | 4 | 2.5 | 145 | 1124 |
| 3 | 8 | 5 | 1.5 | 145 | 1127 |
| 4 | 8 | 5 | 2.5 | 155 | 1117 |
| 5 | 10 | 5 | 2.5 | 140 | 1129 |
| 6 | 10 | 4 | 1.5 | 124 | 1147 |
| 7 | 10 | 4 | 2.5 | 132 | 1136 |
| 8 | 10 | 5 | 1.5 | 132 | 1139 |
| 9 | 6 | 3 | 1 | 120 | 1137 |
| 10 | 6 | 6 | 3 | 180 | 1090 |
| 11 | 6 | 6 | 1 | 156 | 1109 |
| 12 | 6 | 3 | 3 | 144 | 1109 |
| 13 | 12 | 3 | 1 | 144 | 1171 |
| 14 | 12 | 6 | 3 | 189 | 1129 |
| 15 | 12 | 6 | 1 | 209 | 1146 |
| 16 | 12 | 3 | 3 | 198 | 1148 |
| 17 | 9 | 4.5 | 2 | 155 | 1132 |

Example 18. Verification of Efficacy of the Traditional Chinese Medicine Composition for Sober-Up and Hepatic Protection of the Present Invention 1. Material and Method 1.1 Laboratory animals and environment: 50 SPF-grade male Kunming mice (body weight 18-22 g); the experimental environment is shielded environment with a temperature of 23° C. to 24° C. and humidity of 50% to 56%.

1.2 Dosage selection and administration mode of the test sample: The dosage administered to the mice was 0.233 g/kg·bw, 0.467 g/kg·bw, and 1.400 g/kg·bw (equivalent to 5, 10, and 30 times of the recommended dosage for human body, respectively). Blank control group and liver damage model control group were established at the same time. In the preparation of the low, medium, and high dosage test samples, the traditional Chinese medicine composition of Examples 1 to 17 of the present invention were taken respectively, and prepared with distilled water to achieve different concentrations, which respectively were low dosage 11.65 g/L, medium dosage 23.35 g/L, and high dosage 70.00 g/L. The mice were administered intragastrically once a day for 30 consecutive days with a volume of 0.2 ml/10 g·bw. The blank control group and the liver damage model control group were administered with equal volume of distilled water.

1.3 Main Instruments and Reagents:

OLYMPUS AU400 full-automatic biochemical analyzer, 722 spectrophotometer, pipette, thermostat water bath, centrifuge, vortex mixer, tissue homogenizer, malondialdehyde (MDA), reduced glutathione (GSH), and triglyceride (TG).

1.4 Experimental Method:

1.4.1 Animal treatment: According to 1.2, each dosage group was administered intragastrically with the test solution. The blank control and model control groups were administered intragastrically with distilled water, once a day for 30 consecutive days. On day 30, each dosage group and the model control group were administered intragastrically with 50% ethanol (12 ml/kg·bw), resulting in acute liver damage model. The blank control group was administered intragastrically with equal volume of distilled water. The animals were sacrificed after fasting for 16 hours, and subjected to various index determinations and histopathological detection.

1.4.2 Index determinations: liver was taken and prepared into 10% liver homogenate with normal saline to determine the contents of reduced glutathione (GSH) and triglyceride (TG) in the liver tissue. Additionally, liver was prepared into 5% liver homogenate with 0.2 M phosphate buffer solution to determine the content of malondialdehyde (MDA) in the liver tissue. The determination of the contents of GSH and MDA in the liver tissue was conducted according to the instructions of the kits. The TG level in the liver tissue was determined with the OLYMPUS AU400 full-automatic biochemical analyzer.

1.4.3 Histopathological detection: samples were taken from transection of the middle part of the left lobe of mice's liver. Frozen section was obtained and stained by Sudan III. During microscopy, the pathological changes of cells were recorded form one end of the visual field of the liver. The overall tissue section was consecutively observed by 40× objective lens, wherein the distribution, scope and area of lipid droplets in the liver were observed and scored according to the following criteria: 0 score, lipid droplets in liver cells are interspersed and rare; 1 score, liver cells containing lipid droplets are not more than ¼; 2 scores, liver cells containing lipid droplets are not more than ½; 3 scores, liver cells containing lipid droplets are not more than ¾; 4 scores, the liver tissue is almost replaced by lipid droplets.

1.5 Statistics of Experimental Data

Statistic analysis was conducted with Spss 11.0 software, wherein the data were firstly tested for the homogeneity of variance. For the equal variance, one-way ANOVA was employed for overall comparison, and if difference was found, pairwise comparison was conducted using Dunnett method from the averages of various dosage groups, blank control group and one model control group. For unequal variances, appropriate variable conversion of the original data was conducted, and after the requirements for tests with equal variance were met, the statistics were conducted with the converted data. If the purpose of equal variance was still not achieved after the variable conversion, rank-sum test was turned to conduct the statistics. If difference was found in overall comparison, Tamhane's T2 test which does not require an equal variance was employed to conduct the pairwise comparison.

1.6 Judgment of the Results

If the results of the three test indexes including malondialdehyde (MDA), reduced glutathione (GSH) and triglyceride (TG) in liver tissue were positive, or if any two of the three indexes including malondialdehyde (MDA), reduced glutathione (GSH) and triglyceride (TG) were positive and the result of pathological detection was positive, then it can be judged that the test sample has auxiliary protective effect on chemical liver damages.

2. Results 2.1 Effects of the Capsule on the Body Weight of Animals

Wherein, the test results of Example 17 of the present invention are shown in Table 2. The test results of the traditional Chinese medicine composition prepared according to other examples are similar.

TABLE 2

The effect of the traditional Chinese medicine composition of the present invention on body weight of mice

| Groups | Animal number | Initial body weight $\bar{x} \pm s$ (g) | Body weight after intragastric administration for 15 days $\bar{x} \pm s$ (g) | Body weight after intragastric administration for 15 days $\bar{x} \pm s$ (g) | Weight gain $\bar{x} \pm s$ (g) |
|---|---|---|---|---|---|
| Model control group | 10 | 19.73 ± 1.21 | 30.63 ± 1.91 | 36.29 ± 2.65 | 16.56 ± 1.72 |
| Blank control group | 10 | 19.75 ± 1.17 | 29.90 ± 1.90 | 35.56 ± 2.89 | 15.81 ± 1.86 |
| Low dosage group | 10 | 19.88 ± 1.19 | 29.53 ± 2.06 | 36.20 ± 2.86 | 16.32 ± 1.95 |
| Medium dosage group | 10 | 19.83 ± 1.18 | 30.33 ± 2.21 | 36.55 ± 3.23 | 16.72 ± 2.30 |
| High dosage group | 10 | 19.88 ± 1.24 | 29.77 ± 1.67 | 36.78 ± 2.58 | 16.90 ± 1.59 |

The results showed that upon comparison of the body weights of each dosage group with those of the model control group and blank control group, there was no significant difference (P>0.05).

2.2 Effects of the Capsule on MDA, GSH and TG Levels in Liver Tissue.

TABLE 3

Effects of the traditional Chinese medicine composition of the present invention on MDA, GSH and TG levels in liver tissue of mice

| Groups | Animal number | MDA level $\bar{x} \pm s$ (μmol/g liver) | P value | GSH level $\bar{x} \pm s$ (μmol/g liver) | P value | TG level $\bar{x} \pm s$ (μmol/g liver) | P value |
|---|---|---|---|---|---|---|---|
| Model control group | 10 | 1.75 ± 0.22 | — | 9.72 ± 5.69 | — | 0.0333 ± 0.0067 | — |
| Blank control group | 10 | 0.95 ± 0.28 | 0.000 | 23.12 ± 6.37 | 0.000 | 0.0191 ± 0.0068 | 0.000 |
| Low dosage group | 10 | 1.64 ± 0.24 | 0.688 | 12.94 ± 5.93 | 0.540 | 0.0286 ± 0.0057 | 0.298 |
| Medium dosage group | 10 | 1.60 ± 0.26 | 0.464 | 14.93 ± 5.88 | 0.151 | 0.0269 ± 0.0074 | 0.098 |
| High dosage group | 10 | 1.57 ± 0.23 | 0.271 | 16.72 ± 4.90 | 0.032 | 0.0238 ± 0.0054 | 0.007 |

As can be seen from table 3, the MDA and TG levels in the model control group were all higher than those of the blank control group, the GSH level in the model control group was lower than that of the blank control group, and the differences were all significant (P<0.01). In the high dosage group, the TG level was significantly lower than that of the model control group, the GSH level was significantly higher than that of the model control group, and the differences were significant (P<0.05 or P<0.01).

2.3 the Effects of the Traditional Chinese Medicine Composition of the Present Invention on the Histopathology of Liver.

TABLE 4

Effects of the traditional Chinese medicine composition of the present invention on the degree of steatosis of the liver tissue of mice

| Groups | Animal number | \multicolumn{5}{c}{Number of animal having various degrees of lesion} | Degree of change ($\bar{x} \pm s$) | P value (as compared to the model group) |
|---|---|---|---|---|---|---|---|---|
| | | 0 score | 1 score | 2 scores | 3 scores | 4 scores | | |
| Model control group | 10 | 0 | 0 | 1 | 4 | 5 | 3.40 ± 0.70 | — |
| Blank control group | 10 | 7 | 3 | 0 | 0 | 0 | 0.30 ± 0.48 | 0.000 |
| Low dosage group | 10 | 0 | 0 | 4 | 3 | 3 | 2.90 ± 0.88 | 0.353 |
| Medium dosage group | 10 | 0 | 0 | 4 | 4 | 2 | 2.80 ± 0.79 | 0.207 |
| High dosage group | 10 | 0 | 0 | 6 | 5 | 1 | 2.50 ± 0.71 | 0.027 |

As can be seen from Table 4, the degree of hepatic steatosis in the model control group was higher than that of the blank control group, and the difference was significant (P<0.01); the degree of hepatic steatosis in the high dosage group was significantly lower than that of the model control group, and the difference was significant (P<0.05).

In summary, after intragastric administration to mice with the traditional Chinese medicine composition of the present invention at dosages of 0.233 g/kg·bw, 0.467 g/kg·bw, 1.400 g/kg·bw for 30 days, acute liver damage model was established by ethanol. The test sample had no significant effect on the body weight of mice. The hepatic TG level in animals of 1.400 g/kg·bw dosage group was significantly lower than that of the model control group, while the hepatic GSH level was significantly higher than that of the model control group, and the difference was significant (p<0.05 or p<0.01). The degree of hepatic steatosis in animals of 1.400 g/kg·bw dosage group was significantly lower than that of the model control group, and the difference was significant (p<0.05). Thus, it was demonstrated that the test sample had auxiliary protective effects on chemical liver damages.

Example 19. Preparation of Sober-Up and Hepatic Protection Capsule

The formula of the sober-up and hepatic protection capsule is shown in Table 5.

TABLE 5

Formula of the capsule of health care product

| Category | Amount (g) |
|---|---|
| The traditional Chinese medicine composition of Example 17 | 90 |
| Corn starch | 7 |
| Magnesium stearate | 3 |

The traditional Chinese medicine composition of Example 17, corn starch were taken and added into a three dimensional motion mixer, and evenly mixed for no less than 20 minutes. The resultant mixture was granulated with a dry granulation machine. Finally, magnesium stearate was added. The mixture was mixed for 10 min. The materials were discharged after being mixed uniformly. They were filled into 0# or 1# empty gelatin capsules. The load for each capsule was 350 mg.

Example 20. Preparation of Sober-Up and Hepatic Protection Normal Compressed Tablet The formula of the sober-up and hepatic protection normal compressed tablet is shown in Table 6.

TABLE 6

Formula of the capsule of health care product

| Category | Amount (g) |
|---|---|
| The traditional Chinese medicine composition of Example 16 | 85 |
| Microcrystalline cellulose | 10 |
| Sodium carboxymethylcellulose | 1 |
| Magnesium stearate | 2 |
| 7% starch slurry | 2 |

The traditional Chinese medicine composition as prepared in Example 16, corn starch and magnesium stearate were respectively pulverized, sieveed (80 to 100 mesh), and mixed. The resultant mixture was prepared into soft material with 7% starch slurry. Then the soft material was granulated on a screw extrusion granulation machine to obtain the sober-up and hepatic protection normal compressed tablets.

Example 21. Preparation of Sober-Up and Hepatic Protection Dripping Pill

The formula of the dripping pill of health care product is shown in Table 7.

TABLE 7

Formula of the capsule of health care product

| Category | Amount (g) |
|---|---|
| The traditional Chinese medicine composition of Example 14 | 85 |
| PEG6000 | 10 |
| S-40 | 5 |

The traditional Chinese medicine composition of Example 14 was taken and passed through an 80-mesh sieve for later use.

PEG6000 and S-40 were mixed and then heated to 60° C. to melt. Size of the dropping head was adjusted. Dropping was conducted with simethicone or liquid paraffin as the cooling phase. The obtained pills were filtered, washed, and selected to obtain the target pills.

Example 22. Preparation of Sober-Up and Hepatic Protection Chewable Tablet

The formula of the sober-up and hepatic protection chewable tablet is shown in Table 8.

TABLE 8

Formula of the sober-up and hepatic protection chewable tablet

| Names of raw materials and excipients | Amount (g) |
|---|---|
| The traditional Chinese medicine composition of Example 10 | 78 |
| Microcrystalline Cellulose | 20 |
| Mannitol | 2.0 |
| Aspartame | 0.6 |
| Tangerine essence | 0.7 |
| 40% ethanol | q.s. |

The traditional Chinese medicine composition of Example 10, microcrystalline cellulose and mannitol were respectively passed through an 80-mesh sieve, uniformly mixed. The mixture was prepared into a soft material with 40% ethanol (the amount of 40% ethanol to be added was such an amount that the soft material would gather into cluster by hand grasp, but scatter by slight pressure), granulated by a 16-mesh sieve, dried and finished by a 12-mesh sieve. Aspartame and tangerine essence were added. The resultant mixture was then uniformly mixed and compressed into tablets.

Example 23. Preparation of Sober-Up and Hepatic Protection Granules

The formula of the sober-up and hepatic protection granules is shown in Table 9.

TABLE 9

Formula of the sober-up and hepatic protection granules

| Names of raw materials and excipients | Amount (g) |
|---|---|
| The traditional Chinese medicine composition of Example 8 | 90 |
| Sucrose | 5 |
| β-cyclodextrin | 5 |

Sucrose and the traditional Chinese medicine composition of Example 8 were pulverized, passed through an 80 to 100 mesh sieve, and mixed with 3% by mass of distilled water. The resultant mixture was passed through a 14 to 22 mesh sieve (plate) by extrusion and prepared into uniform granules, which were dried to obtain the sober-up and hepatic protection granules.

Example 24. Preparation of Sober-Up and Hepatic Protection Syrup

The formula of the sober-up and hepatic protection syrup is shown in Table 10.

TABLE 10

Formula of the sober-up and hepatic protection syrup

| Names of raw materials and excipients | Amount (g) |
|---|---|
| The traditional Chinese medicine composition of Example 6 | 50 |
| Sucrose | 50 |
| Water | 100 |
| Potassium sorbate | 0.3 |

The traditional Chinese medicine composition of Example 6, sucrose and water were mixed. The resultant mixture was boiled and filtered. After that potassium sorbate was added to prepare the sober-up and hepatic protection syrup.

Example 25. Preparation of Sober-Up and Hepatic Protection Oral Liquid

The formula of the sober-up and hepatic protection oral liquid is shown in Table 11.

TABLE 11

Formula of the sober-up and hepatic protection oral liquid

| Names of raw materials and expicients | Amount (g) |
|---|---|
| The traditional Chinese medicine composition of Example 3 | 50 |
| Simple syrup | 25 (mL) |
| Water | 75 |
| Potassium sorbate | 0.3 |

The traditional Chinese medicine composition of Example 3, simple syrup and water were mixed. The resultant mixture was then boiled and filtered. After that potassium sorbate was added to obtain the sober-up and hepatic protection oral liquid.

Example 26. The Pharmacodynamic Verification of the Sober-Up and Hepatic Protection Capsule of the Present Invention 40 healthy volunteers aged 20 to 40 (including 25 males and 15 females) with normal blood pressure, blood lipid, blood sugar and without other diseases were randomly selected. The volunteers consecutively took the sober-up and hepatic protection capsule as prepared in Example 19 for 1 month. At the end of two weeks and 1 month, they were investigated for their capacity for liquor and symptoms after wine drinking.

After administration for 1 month, none of the volunteers developed uncomfortable symptoms. Their blood pressure, blood lipid and blood sugar were stable without significant changes.

After administration for 1 month, the volunteers were tested for their capacity for liquor with white spirit, yellow wine, grape wine/red wine, beer and foreign wine, wherein 18% of volunteers believed that their capacity for liquor had been significantly improved, 50% of them believed that their capacity for liquor had been improved but not significantly, 20% of them did not know whether their capacity for liquor had been improved, and 12% of them believed that their capacity for liquor had not been improved at all. Totally 27 volunteers (68% of all the volunteers) believed that their capacity for liquor had been improved to some extent after administration of the sober-up and hepatic protection capsule. After administration for 2 weeks and 1 month, the improved capacities for various wines of the volunteers are shown in Table 12:

TABLE 12

The improved capacities for various wines of the volunteers

| | White spirit | Yellow wine | Grape wine/ red wine | Beer | Foreign wine |
|---|---|---|---|---|---|
| After administration for 2 weeks | 20% | 5% | 11% | 14% | 8% |
| After administration for 1 month | 22% | 5% | 13% | 13% | 20% |

The results showed that, in all the volunteers who felt that their capacity for liquor had been improved, the improved capacity for white spirit was relatively significant. Meanwhile, the investigation results of symptoms of volunteers after wine drinking are shown in Table 13:

TABLE 13

The investigation results of symptoms of volunteers after wine drinking

| | Dizziness and fullness in head | Blush | Vomit | Parched mouth and scorched tongue | Trance, smug | Stomachache and gastrectasia | Get drunk and lethargy | Excitement, loquacity | systemic fever |
|---|---|---|---|---|---|---|---|---|---|
| After administration for 2 weeks | 85% | 82% | 81% | 73% | 71% | 64% | 63% | 58% | 38% |
| After administration for 1 month | 92% | 89% | 82% | 89% | 72% | 69% | 74% | 100% | 62% |

The results showed that, after administration of the sober-up and hepatic protection capsule for 2 weeks, symptoms of dizziness, fullness in head, blush, vomit, parched mouth, scorched tongue, etc. were significantly improved, while the symptom of systemic fever was not improved significantly. After administration for 4 weeks, the improvement was more significant.

The investigation results of symptoms of the volunteers when they waked up in the next day after wine drinking are shown in Table 14:

TABLE 14

The investigation results of symptoms of the volunteers when they waked up in the next day after wine drinking

| | Dizziness and fullness in head | Parched mouth and scorched tongue, sore throat | Trance, fatigue | Stomach discomfort, abdominal pain and diarrhea | Red and swollen eyes and blood shot eyes |
|---|---|---|---|---|---|
| After administration for 2 weeks | 86% | 80% | 77% | 80% | 69% |
| After administration for 1 month | 89% | 88% | 81% | 86% | 71% |

The results showed that, after administration of the product for 2 weeks, all the symptoms were significantly improved when the volunteers waked up in the next day after wine drinking, wherein it was especially significant for the symptoms of dizziness, fullness in head, stomach discomfort, the discomfort of mouth, tongue and throat, etc. After administration for 4 weeks, the improvement was more significant.

The investigation results showed that, after administration of the sober-up and hepatic protection capsule of Example 19 of the present invention, the capacity for liquor had been improved to some extent, and the symptoms after wine drinking and the symptoms after waking up in the next day were all improved.

Example 27. Pharmacodynamic Verification of the Sober-Up and Hepatic Protection Capsule of the Present Invention 60 healthy volunteers aged 20 to 40 (including 43 males and 17 females) with normal blood pressure, blood lipid, blood sugar and without other diseases were randomly selected. After administration of the sober-up and hepatic protection dropping pills as prepared in Example 21, the volunteers were randomly divided into 3 groups and drank wine after administration for 15 minutes, 30 minutes and 60 minutes. The symptoms after wine drinking were investigated. After administration, none of the volunteers developed uncomfortable symptoms, and their blood pressure, blood lipid and blood sugar were stable without significant changes. The investigation results are shown in Table 15:

TABLE 15

The improved capacity for liquor of the volunteers

| | Significant improvement in capacity for liquor | Less significant improvement in capacity for liquor | No improvement in capacity for liquor, weakened reactions after wine drinking | No improvement in capacity for liquor at all, and no relief in the reactions after wine drinking |
|---|---|---|---|---|
| After administration for 15 min | 5% | 15% | 50% | 30% |
| After administration for 30 min | 0% | 15% | 65% | 20% |
| After administration for 60 min | 5% | 20% | 60% | 15% |

The investigation results showed that, after administration of the sober-up and hepatic protection dropping pills of Example 21 of the present invention, the proportion for volunteers having improved capacity for liquor was not high, but the proportion for ones having weakened symptoms after wine drinking was high.

The above are merely preferred embodiments of the present invention. It should be noted that, for the ordinary skilled in the art, several improvements and modifications can also be made without departing from the principle of the present invention, which improvements and modifications should also be deemed to be within the protection scope of the present invention.

The invention claimed is:

1. A method for preparing a traditional Chinese medicine composition, which is made from raw materials in the following parts by mass: 6 to 12 parts of Radix Puerariae, 3 to 6 parts of Semen Hoveniae, and 1 to 3 parts of Fructus Gardeniae,
   wherein the method comprises: extracting Radix Puerariae, Semen Hoveniae and Fructus Gardeniae with water, concentrating, drying, and pulverizing the extract, to obtain the traditional Chinese medicine composition.

2. The preparation method according to claim 1, wherein the mass of water is 8 to 12 times the sum of the mass of Radix Puerariae, Semen Hoveniae and Fructus Gardeniae.

3. The preparation method according to claim 1, wherein the extraction is carried out by decoction, and the decoction is conducted twice, each for 2 hours.

4. The preparation method according to claim 1, wherein the concentration is conducted to achieve a relative density of 1.0 to 1.5.

5. The method according to claim 1, wherein the traditional Chinese medicine composition is made from raw materials in the following parts by mass: 8 to 10 parts of Radix Puerariae, 4 to 5 parts of Semen Hoveniae, and 1.5 to 2.5 parts of Fructus Gardeniae.

6. The method according to claim 1, wherein the traditional Chinese medicine composition is made from raw materials in the following parts by mass: 9 parts of Radix Puerariae, 4.5 parts of Semen Hoveniae, and 2 parts of Fructus Gardeniae.

* * * * *